United States Patent
Shibuya et al.

(10) Patent No.: US 10,086,313 B2
(45) Date of Patent: Oct. 2, 2018

(54) SEPARATION DEVICE AND SEPARATION METHOD

(71) Applicant: HITACHI, LTD., Tokyo (JP)

(72) Inventors: Keisuke Shibuya, Tokyo (JP); Yasuhiko Tada, Tokyo (JP); Takeyuki Kondo, Tokyo (JP); Sei Murakami, Tokyo (JP)

(73) Assignee: HITACHI, LTD., Tokyo (JP)

( * ) Notice: Subject to any disclaimer, the term of this patent is extended or adjusted under 35 U.S.C. 154(b) by 1 day.

(21) Appl. No.: 14/897,844

(22) PCT Filed: Jun. 19, 2014

(86) PCT No.: PCT/JP2014/066232
§ 371 (c)(1),
(2) Date: Dec. 11, 2015

(87) PCT Pub. No.: WO2015/001963
PCT Pub. Date: Jan. 8, 2015

(65) Prior Publication Data
US 2016/0136543 A1 May 19, 2016

(30) Foreign Application Priority Data
Jul. 5, 2013 (JP) ................................. 2013-142061

(51) Int. Cl.
*B01D 15/08* (2006.01)
*B01D 15/18* (2006.01)
(Continued)

(52) U.S. Cl.
CPC ............. *B01D 15/22* (2013.01); *B01D 15/08* (2013.01); *B01D 15/1885* (2013.01);
(Continued)

(58) Field of Classification Search
CPC ................ B01D 15/08; B01D 15/1821; B01D 15/1885; B01D 15/20; B01D 15/22; C07K 1/22; G01N 2030/8813
See application file for complete search history.

(56) References Cited

U.S. PATENT DOCUMENTS 4,422,881 A * 12/1983 Devos ..................... C13B 20/14
127/46.1
4,764,276 A * 8/1988 Berry ..................... B01D 53/06
210/264
(Continued)

FOREIGN PATENT DOCUMENTS

JP        2010271300 A        12/2010
JP        2011214837 A        10/2011
(Continued)

OTHER PUBLICATIONS

English Language Translation of JP 2011-214837 to Iwakura (2011) (obtained from JPO Feb. 2017).*
(Continued)

*Primary Examiner* — Lucas A Stelling
(74) *Attorney, Agent, or Firm* — Oliff PLC

(57) ABSTRACT

An object of the present invention is to separate a material to be separated at a low cost and constant accuracy when the material to be separated is separated from a mobile phase containing the material to be separated through the passing of the mobile phase through a stationary phase, even if the mobile phase has a large volume. A separation device characterized in that a separation column provided with a stationary phase having a volume capable of processing the entire volume of a mobile phase containing a material to be separated is provided, the separation column is replaceable, and the usage count of the stationary phase reaches a lifetime count through the processing of one batch.

2 Claims, 9 Drawing Sheets

(51) Int. Cl.
*B01D 15/20* (2006.01)
*B01D 15/22* (2006.01)
*G01N 30/88* (2006.01)
*C07K 1/22* (2006.01)

(52) U.S. Cl.
CPC .......... *B01D 15/20* (2013.01); *B01D 15/1821* (2013.01); *C07K 1/22* (2013.01); *G01N 2030/8813* (2013.01)

(56) References Cited

U.S. PATENT DOCUMENTS

| | | | | |
|---|---|---|---|---|
| 4,806,250 | A | * | 2/1989 | Takata ............... B01D 15/1871 210/198.2 |
| 6,080,318 | A | * | 6/2000 | Gumm ............... B01D 15/1885 210/198.2 |
| 2010/0176058 | A1 | * | 7/2010 | Bryntesson ........ B01D 15/1828 210/659 |

FOREIGN PATENT DOCUMENTS

| | | |
|---|---|---|
| WO | 2008/127087 A1 | 10/2008 |
| WO | 2008/153472 A1 | 12/2008 |

OTHER PUBLICATIONS

Sep. 30, 2014 International Search Report issued in International Patent Application No. PCT/JP2014/066232.
Feb. 9, 2017 Extended European Search report issued in European Patent Application No. 14820358.1.

\* cited by examiner

ARROW: LIQUID
FLOW DIRECTION

VOLUME: Vc·N

VOLUME: Vc·N

SEPARATION DEVICE AND SEPARATION METHOD

TECHNICAL FIELD

The present invention relates to a separation device and a separation method for separating a material to be separated from a mobile phase by passing the mobile phase containing the material to be separated through a stationary phase.

BACKGROUND ART

The separation device for separating the material to be separated from the mobile phase by passing the mobile phase containing the material to be separated through the stationary phase is used, for example, when separating useful materials produced by cell culture. For example, antibody drugs, which are the useful materials, can be obtained by culturing animal cells having antibody producibility and by separating and purifying antibodies secreted into a culture solution. That is, the useful materials such as antibody drugs are separated and purified using chromatography after removing cells from the culture solution. Meanwhile, when producing a given useful material by using microorganisms, the useful material often accumulates in the cells. In this case, solids are removed from the solution after the cells are disrupted, and then the useful material is separated and purified using chromatography.

The antibody drugs are generally produced through a clarification step, a capture step, an intermediate purification step, and a polishing step. In this production method, different separation devices, i.e., chromatographic methods are used in each step depending on the type of the antibody of interest. However, it is common that purity of the antibody is increased and selectivity of the antibody of interest is increased in a stepwise manner.

The clarification step is to remove the solids or proteins other than the antibody from the culture solution as much as possible. Since culture solution components such as serum, ascites fluid, and hybridoma cell culture solution are different and inclusions are also different for each type of the antibodies, the clarification is performed by using different methods such as salting-out, filtration with a filter, centrifugal separation.

Further, in the capture step, affinity chromatography is usually used. When the antibody of interest is IgG, very high specific affinity chromatography using Protein A or Protein G as a ligand is used, and it is possible to perform purification to a purity of 90% or more in one step. On the other hand, when the antibody of interest is, for example, IgM or IgY, which is an antibody having low affinity for Protein A and Protein G, affinity chromatography utilizing thiophilic interaction is used. Further, when the antibody of interest is IgA, IgD or IgE, affinity chromatography with a column immobilized with a secondary antibody recognizing the antibody is used, because blood concentration thereof is low and there is no high affinity ligand therefor. In the capture step, processing speed and processing capacity are important, and it is required to rapidly separate and concentrate the antibody of interest from a crude state of a cell extract or the like. It is for facilitating subsequent steps.

Next, in the intermediate purification step, contaminants recovered along with the antibody of interest in the capture step are removed. In this step, since an amount of treatment solution is large, ion exchange chromatography with large capacity is generally used. Note that, when the amount of treatment solution is small, the capture step and the intermediate purification step can be performed in one step.

The last polishing step is a step for separating the contaminants remaining slightly by using high performance column, to obtain final purified antibody. In the polishing step for obtaining the antibody of interest, gel permeation chromatography with a high resolution column is generally used. By using gel permeation chromatography, it is possible to perform buffer exchange together with removal of low-molecular materials inhibiting structural analysis.

In biopharmaceutical production, it is typical that a plurality of culture tanks with a volume of about 10 $m^3$ are installed, and after culturing animal cells in the culture tanks, a large amount of culture solution (10 $m^3$ or more per one batch) containing biopharmaceuticals (for example, antibodies) is processed. As a particular problem in a process of such a large amount of culture solution, the capture step using affinity chromatography can be mentioned. A protein (for example, Protein A), which is used in the affinity chromatography and is specifically bound to biopharmaceuticals, is very expensive. Therefore, the column with the protein is reused repeatedly for each culture batch. However, reuse of the column has a possibility that various components in the previous process remain, as well as a possibility of column degradation. Due to these possibilities, there is a possibility that purification quality of biopharmaceuticals varies among the culture batches.

In general, an affinity purification column for producing biopharmaceuticals is very large with a diameter of about 1 m and a bed height of several tens cm, and an equipment with the affinity column requires a certain space. Meanwhile, since the culture solution to be treated has a large volume of 10 $m^3$ or more, it is necessary to repeat the capture step many times to process a batch of culture solution even when using the above large purification column. The capture step includes steps of (I) column equilibration, (II) target material adsorption, (III) washing, (IV) target material elution, and (V) column regeneration. A step of processing the culture solution is the step of (II) target material adsorption, and the steps of (I) and (III) to (V) are in a wait state for processing the culture solution. In order to process a large volume of culture solution, the steps of (I) to (V) must be repeated many times, and the wait state is long, and as a result, processing time in the capture step is increased. For example, in Patent Document 1, in order to eliminate waiting time, a method in which plural columns are installed, and the step of (II) target material adsorption for processing the culture solution is continuously performed by shifting the capture step in each column has been studied. However, in this method, it is necessary to ensure a large equipment space to install the plural columns, and there is a problem that cost of column filler is increased.

CITATION LIST

Patent Literature

{Patent Document 1}
Japanese Patent Publication No. 2011-214837

SUMMARY OF INVENTION

Technical Problem

As described above, an object of the present invention is to provide a separation device and a separation method capable of separating a material to be separated even from a large volume of mobile phase at a low cost and constant accuracy, when separating the material to be separated from the mobile phase by passing the mobile phase containing the material to be separated through the stationary phase.

Solution to Problem

The present inventors have intensively studied in order to achieve the above-described object, and as a result, have found that it is possible to separate a target material at constant accuracy per batch by providing a stationary phase having a volume required to process a predetermined volume of mobile phase and by replacing the stationary phase, as well as it is possible to reduce processing time for processing multiple batches, and thus have completed the present invention.

That is, the present invention includes the followings.

(1) A separation device characterized by including a separation column provided with a stationary phase having a volume capable of processing an entire volume of mobile phase containing a material to be separated, the separation column being replaceable, wherein a usage count of the stationary phase reaches a lifetime count by one batch process.

(2) The separation device according to (1), characterized in that the separation column is composed of plural columns provided with the stationary phase, and a total volume of the stationary phase filled in the plural columns is a volume capable of processing the entire volume of the mobile phase containing the material to be separated.

(3) The separation device according to (2), characterized by further including a plurality of pipes respectively connected to each of the plural columns, a plurality of switching valves respectively provided on the plurality of pipes, and a control device for controlling communications between the pipes by the plurality of switching valves.

(4) The separation device according to (2), characterized in that a total of column bed heights of the plural columns is a column bed height when the stationary phase having the above volume is a single column.

(5) The separation device according to (1), characterized in that the volume of the stationary phase is determined based on a total amount of the material to be separated contained in the mobile phase, and a maximum adsorption capacity of the stationary phase.

(6) A separation method characterized by including a step of supplying a mobile phase to a separation column provided with a stationary phase having a volume capable of processing an entire volume of mobile phase containing a material to be separated, the separation column being replaceable, wherein a usage count of the stationary phase reaches a lifetime count by one batch process, and a step of recovering the material to be separated from the stationary phase after processing the entire volume of the mobile phase, wherein the used separation column is replaced after the capture step.

(7) The separation method according to (6), characterized in that the separation column is composed of plural columns provided with the stationary phase, and a total volume of the stationary phase filled in the plural columns is a volume capable of processing the entire volume of the mobile phase containing the material to be separated, wherein the mobile phase is sequentially supplied to the plural columns.

(8) The separation method according to (7), characterized in that a plurality of pipes are respectively connected to each of the plural columns, a plurality of switching valves are respectively provided on the plurality of pipes, and a control device controls communications between the pipes by the plurality of switching valves.

(9) The separation method according to (7), characterized in that a total of column bed heights of the plural columns is a column bed height when the stationary phase having the above volume is a single column.

(10) The separation method according to (6), characterized in that the volume of the stationary phase is determined based on a total amount of the material to be separated contained in the mobile phase, and a maximum adsorption capacity of the stationary phase.

(11) A material production device characterized by including a tank for storing the mobile phase containing the material to be separated, and the separation column which is connected to the tank and is provided with a stationary phase having a volume capable of processing an entire volume of mobile phase stored in the tank, the separation column being replaceable, wherein a usage count of the stationary phase reaches a lifetime count by one batch process.

(12) The material production device according to (11), characterized in that the separation column is composed of plural columns provided with the stationary phase, and a total volume of the stationary phase filled in the plural columns is a volume capable of processing the entire volume of the mobile phase containing the material to be separated.

(13) The material production device according to (12), characterized by further including a plurality of pipes respectively connected to each of the plural columns, a plurality of switching valves respectively provided on the plurality of pipes, and a control device for controlling communications between the pipes by the plurality of switching valves.

(14) The material production device according to (12), characterized in that a total of column bed heights of the plural columns is a column bed height when the stationary phase having the above volume is a single column.

(15) The material production device according to (11), characterized in that the volume of the stationary phase is determined based on a total amount of the material to be separated contained in the mobile phase, and a maximum adsorption capacity of the stationary phase.

Advantageous Effects of Invention

With a separation device and a separation method according to the present invention, it is possible to separate a target material at constant accuracy per batch of mobile phase to be processed. Therefore, by using the separation device according to the present invention, it is possible to obtain a high quality target material of little variation in quality.

DESCRIPTION OF EMBODIMENTS

Figure 1:
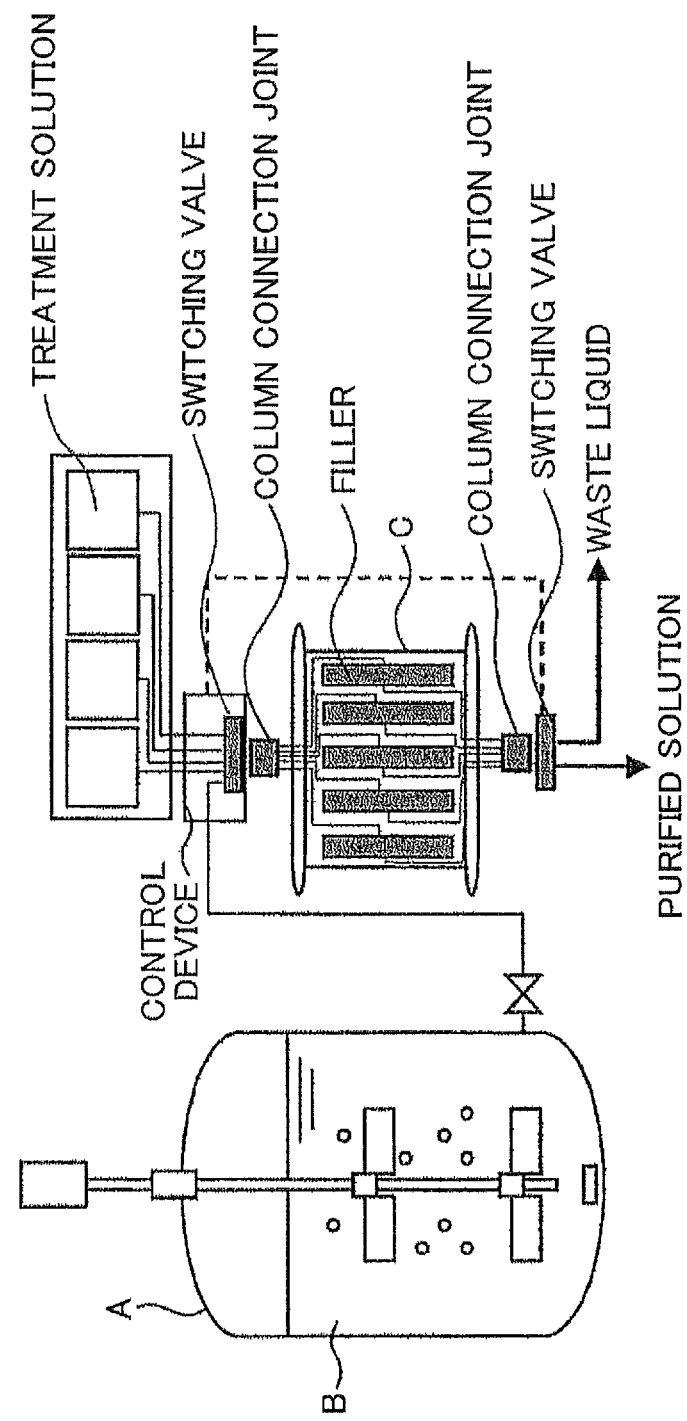
FIG. 1 is a schematic configuration diagram showing an example of a separation device according to the present invention.

Hereinafter, the present invention will be described in detail. As shown in FIG. 1, a separation device according to the present invention includes a separation column C filled with a stationary phase therein. When supplying a solution B (mobile phase) stored in a tank A to the separation column C, a material to be separated contained in the solution is captured by the stationary phase in the separation column C. Then, when supplying an eluent to the separation column C, the material captured by the stationary phase is recovered from the separation column C. The stationary phase filled in the separation column C has a volume capable of processing an entire volume of the solution (mobile phase) to be processed, that is, a volume to reach a lifetime count by one batch process. Therefore, with the separation device according to the present invention, it is possible to reduce processing time for processing multiple batches by replacing the separation column C per batch of the solution B to be processed, as well as to prevent variation of separation accuracy caused by degradation or the like of the stationary phase in the separation column C. Since the separation column and a separation control device portion are separated by a column connection joint portion, replacement of the separation column C can be easily performed by simply removing the column connection joint.

Here, one batch means a predetermined volume of solution obtained by one batch culture, for example when producing a target material by cell culture. Note that, one batch is not limited to the entire volume of the solution obtained by one batch culture, but may be one half of the solution obtained by one batch culture, a solution obtained by one fed-batch culture, or one half of the solution obtained by one fed-batch culture.

Here, the lifetime count of the stationary phase means the number of times that a recovered amount of the target material by the stationary phase is reduced to a predetermined rate, and for example, may be set to the number of times that the recovered amount of the target material is reduced to 10%, 20%, 30%, 40%, 50%, 60%, 70%, 80%, 90%, or 95%. In particular, it is preferable that the lifetime count is set to the number of times that the recovered amount of the target material is reduced to 95%, it is more preferable that the lifetime count is set to the number of times that the recovered amount of the target material is reduced to 90%, it is most preferable that the lifetime count is set to the number of times that the recovered amount of the target material is reduced to 80%.

Hereinafter, an example of the separation device according to the present invention will be described more specifically. As described above, the separation device means a device for separating a specific material from other materials in the mobile phase by capturing the specific material in the mobile phase on the stationary phase by passing the mobile phase through the stationary phase. The separation device is referred to as a purification device in some cases, and is synonymous with a so-called chromatography device. The separation device may be any one of a so-called partition chromatography, adsorption chromatography, molecular exclusion chromatography, ion exchange chromatography and affinity chromatography. In the following example, a system for separating a protein containing an antibody utilized in pharmaceuticals or the like from a cell culture solution will be described. However, the separation device according to the present invention is not limited to this example, and the material to be separated may be any materials.

<Separation Device>

Figure 2:
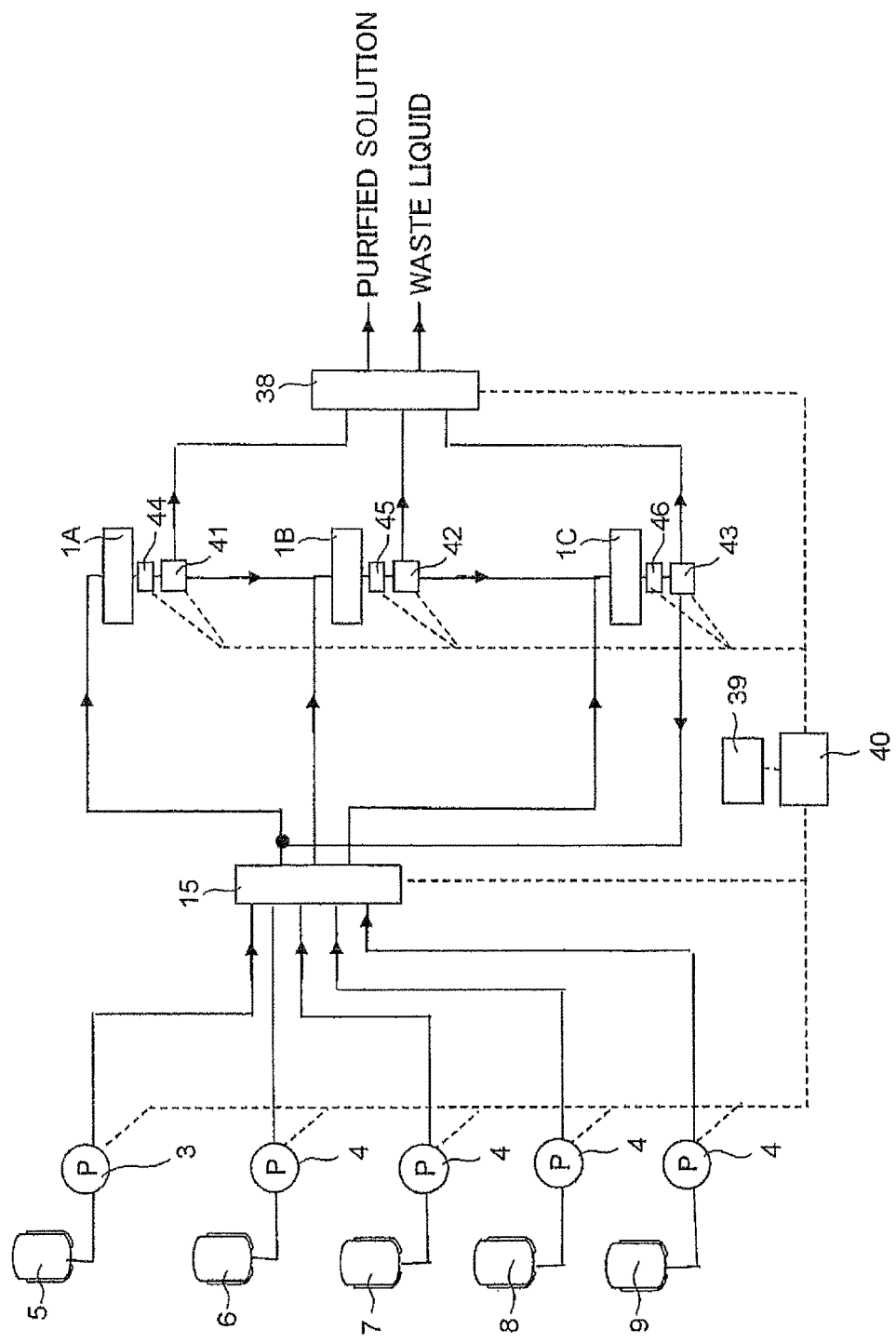
FIG. 2 is an example of a configuration diagram of a continuous affinity purification device (3 columns)
Figure 3:
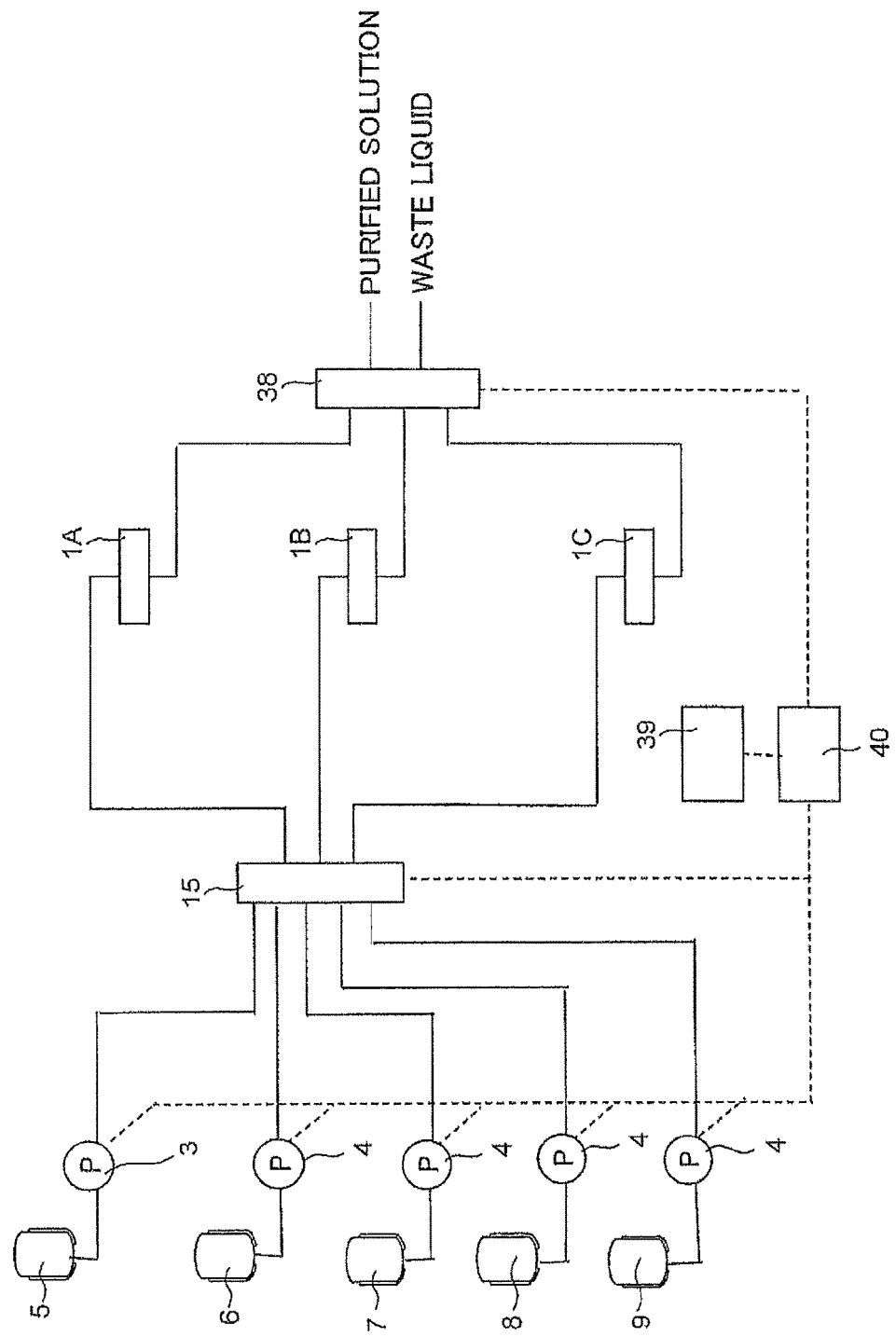
FIG. 3 is another example of a configuration diagram of a continuous affinity purification device (3 columns)

Preferred embodiments of the separation device according to the present invention are shown in FIGS. 2 and 3. The separation device shown in FIGS. 2 and 3 is composed of three affinity packed columns 1A, 1B, and 1C (also referred to as separation columns 1A, 1B and 1C) for continuously processing a solution (mobile phase, sample solution) containing the material to be separated, various solutions used for separation process, pumps for feeding the solutions, and the like. Note that, in the separation device, the number of the packed columns is not limited to three, and it is enough that there are two or more packed columns as necessary as shown in FIG. 3. Here, device configurations with three packed columns (FIGS. 2 and 3) will be described in detail.

A separation device shown in FIG. 2 is composed of three separation columns 1A, 1B and 1C connected in series, five liquid feed pumps 3 and 4, five solution reservoirs 5, 6, 7, 8 and 9, a switching valve 15 (flow path switching unit), and pipes connecting them. The columns connected in series are configured such that an upstream and downstream thereof are connected through pipes, to allow circulation therethrough. An upstream of each column can be in fluid communication with the various solution reservoirs through the switching valve 15. A downstream of each column is configured to be in fluid communication with a switching valve 38 through switching valves 41 to 43, and is configured to be connected from the switching valve 38 to a purified solution pipe or a waste liquid pipe.

Various solutions stored in the reservoirs 5, 6, 7, 8 and 9 are fed to the switching valve 15 by driving the liquid feed pumps 3 and 4. The switching valve 15 performs switching of flow paths so that the various solutions are fed to the appropriate separation columns 1A, 1B and 1C according to the steps shown in FIG. 6, which will be described later in detail. In order to simultaneously perform processes in all the separation columns 1A, 1B and 1C, the switching valve 15 is configured so that all combinations of one-to-one flow path connections from the various solutions to each of the separation columns 1A, 1B and 1C can be performed. However, when there is a solution which is not fed to each column in a step, the solution is not fed (the liquid feed pump 3 or 4 is not driven).

The solution coming out from each of the separation columns 1A, 1B and 1C is recovered as a purified solution through a recovery pipe when it is the target material separated by elution solution, and it is recovered as a waste liquid through the waste liquid pipe when it is not the target material. Combinations between each of the separation columns 1A, 1B, 1C and each of the pipes (purified solution pipe and waste liquid pipe) are selected by the switching valve 38 according to the steps shown in FIG. 6. The switching valves 15 and 38 are configured such that all combinations of the flow paths between each of the separation columns 1A, 1B, 1C and each of the pipes are realized. Control of the pumps 3, 4, and the switching valves 15, 38 according to the steps shown in FIG. 6 can be performed by a control device 40 in accordance with a control program which is stored in advance in a computer 39. Thus, with this separation device, it is possible to continuously process the sample solution, to continuously recover only the target material. It is also possible to detect absorbance by UV device in order to confirm whether the target material is properly recovered.

With this separation device, a simulated moving bed process can be performed, and specific steps will be described below. Step 1: a feed solution (reservoir 5) containing at least one target compound is passed across the separation column 1A, and an effluent is moved from the separation column 1A to the separation column 1B. Step 2: the switching valve 15 is controlled so that the feed solution (reservoir 5) is fed to the separation column 1B, and a wash solution (reservoir 6) is passed across the separation column 1A to which the target compound is bound. Step 3: a wash solution effluent (downstream of the separation column 1A) is moved to the separation column 1C, and then an effluent from the separation column 1B is moved to the separation column 1C. Step 4: the separation column 1A is regenerated. Step 5: the feed solution (reservoir 5) is directed to the separation column 1C, and the wash solution (reservoir 6) is passed across the separation column 1B to which the target compound is bound. Step 6: a wash solution effluent (downstream of the separation column 1B) is moved to the separation column 1A, and then an effluent from the separation column 1C is moved to the separation column 1A. Step 7: the separation column 1B is regenerated. Step 8: the feed solution (reservoir 5) is directed to the separation column 1A, and the wash solution (reservoir 6) is passed across the separation column 1C to which the target compound is bound. Step 9: a wash solution effluent (downstream of the separation column 1C) is moved to the separation column 1B, and then the effluent from the separation column 1A is moved to the separation column 1B. Step 10: the separation column 1C is regenerated. Then, Steps 2 to 10 are repeated according to the steps shown in FIG. 6. Here, at least one material to be separated is recovered in Step 4, Step 7, and/or Step 10.

Meanwhile, it may be a separation device shown in FIG. 3. The separation device is composed of three separation columns 1A, 1B and 1C connected in parallel (columns connected in series is regarded as one column), five liquid feed pumps 3 and 4, five solution reservoirs 5, 6, 7, 8 and 9, a switching valve 15 (flow path switching unit), and pipes connecting them. The various solutions stored in the reservoirs 5, 6, 7, 8 and 9 are fed to the switching valve 15 by driving the liquid feed pumps 3 and 4. The switching valve 15 performs switching of flow paths so that the various solutions are fed to the appropriate separation columns 1A, 1B and 1C according to the steps shown in FIG. 6, which will be described later in detail. In order to simultaneously perform processes in all the separation columns 1A, 1B and 1C, the switching valve 15 is configured so that all combinations of one-to-one flow path connections from the various solutions to each of the separation columns 1A, 1B and 1C can be performed. However, when there is a solution which is not fed to each column in a step, the solution is not fed (the liquid feed pump 3 or 4 is not driven).

The solution coming out from each of the separation columns 1A, 1B and 1C is recovered as a purified solution through the recovery pipe when it is the target material separated by the elution solution, and it is recovered as a waste liquid through the waste liquid pipe when it is not the target material. Combinations between each of the separation columns 1A, 1B, 1C and each of the pipes (purified solution pipe and waste liquid pipe) are selected by the switching valve 38 according to the steps shown in FIG. 6. The switching valves 15 and 38 are configured such that all combination of the flow paths between each of the separation columns 1A, 1B, 1C and each of the pipes are realized. Control of the pumps 3, 4, and the switching valves 15, 38 according to the steps shown in FIG. 6 can be performed by the control device 40 in accordance with a control program which is stored in advance in the computer 39. Thus, with this separation device, it is possible to continuously process the sample solution, to continuously recover only the target material. It is also possible to detect absorbance by UV device in order to confirm whether the target material is properly recovered.

Figure 4:
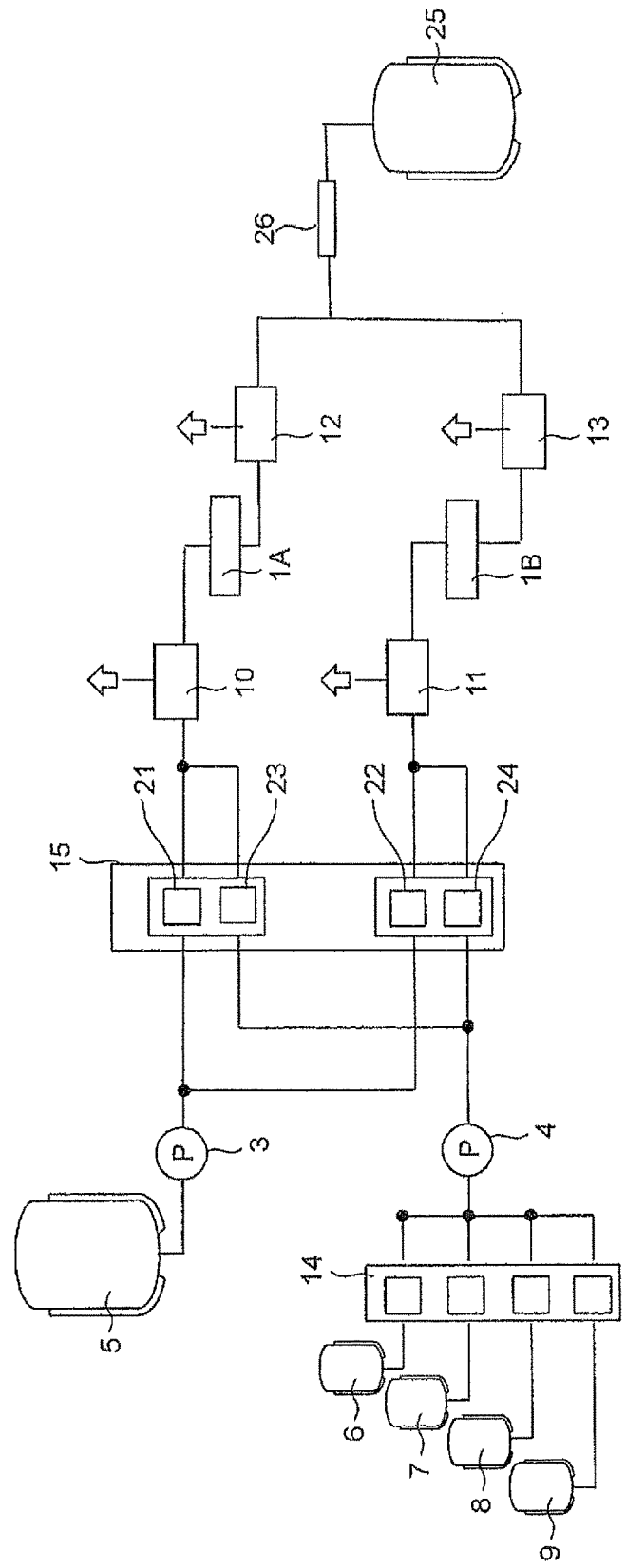
FIG. 4 is an example of a configuration diagram of a continuous affinity purification device (2 columns)
Figure 5:
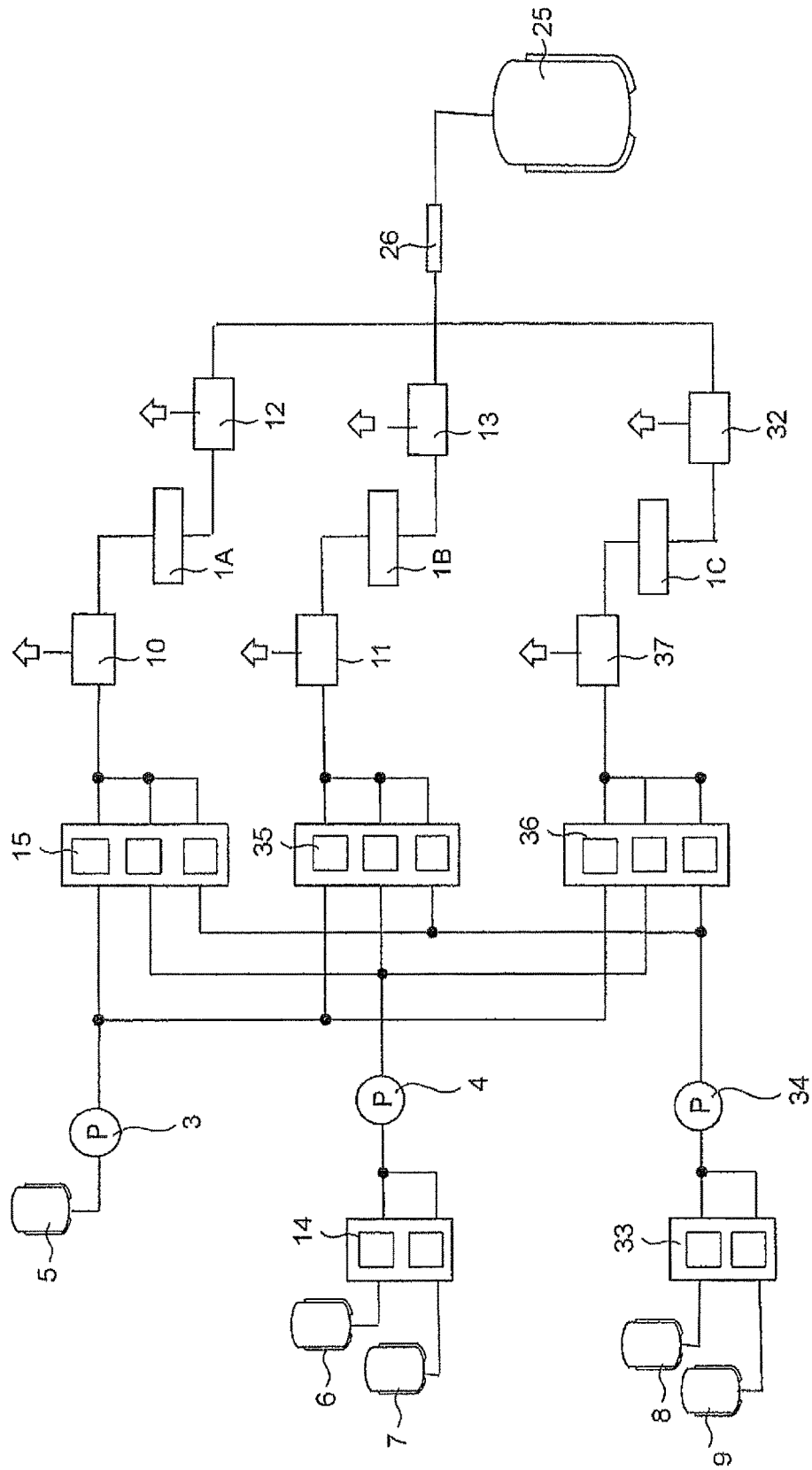
FIG. 5 is another example of a configuration diagram of a continuous affinity purification device (3 columns)

FIG. 4 shows an example of a separation device including two separation columns 1A and 1B, and FIG. 5 shows an example of a separation device including three separation columns 1A, 1B and 1C, and the separation device further includes three liquid feed pumps 3, 4 and 34.

The separation device shown in FIG. 4 is composed of two separation columns (column 1A and column 1B), two liquid feed pumps (pump 3 and pump 4), solution reservoirs (reservoir 5, reservoir 6, reservoir 7, reservoir 8 and reservoir 9), flow path switching units (switching valve 10, switching valve 11, switching valve 12, switching valve 13, selection valve 14, selection valve 15), and pipes connecting them.

A solution stored in the reservoir 5 can be fed by the pump 3, and can be fed to a pipe on a switching valve 21 side or a pipe on a switching valve 22 side by control of the selection valve 15. Solutions stored in the reservoirs 6, 7, 8 and 9 can be fed by the pump 4, and a solution which is fed to a pipe connected to the pump 4 can be selected by control of the selection valve 14. The solution fed to the pump 4 can be selected whether it is fed to a pipe on a switching valve 23 side or a pipe on a switching valve 24 side by control of the selection valve 15. In selection of the selection valve 15, when the pipe from the pump 3 is selected to the switching valve 21 side, the pipe from the pump 4 is selected to the switching valve 24 side at the same time, or when the pipe from the pump 3 is selected to the switching valve 22 side, the pipe from the pump 4 is selected to the switching valve 23 side at the same time.

Further, the switching valve 10 selects a pipe on the column 1A side or a pipe on a waste liquid side, and the switching valve 11 selects a pipe on the column 1B side or a pipe on the waste liquid side. The column 1A is connected to the switching valve 12 through a pipe on the opposite side of the switching valve 10. In addition, the column 1B is connected to the switching valve 13 through a pipe on the opposite side of the switching valve 11. The switching valves 12 and 13 select a pipe on a recovery vessel 25 side or a pipe on the waste liquid side.

In the separation device described above, all of the pumps and the flow path switching units (switching valves) are controlled by the control device programmed with liquid feed conditions such as a feed timing, a feed rate and a feed time. That is, by operating the pumps and the flow path switching units in accordance with a predetermined order by the control device, it is possible to perform a separation operation automatically and continuously. Further, the type of the reservoirs connected to the pump 4 is four types in the example of FIG. 4, but it may be more or less than this.

In FIG. 4, the switching valves 10 and 11 disposed immediately upstream of the columns 1A and 1B respectively allow the solutions passing through the columns 1A and 1B to flow to the waste liquid side in advance, and it is possible to minimize mixing of the solutions before and after when replacing the solutions passing through the columns 1A and 1B. The switching valves 12 and 13 disposed immediately downstream of the columns 1A and 1B can respectively select whether the solutions coming out from the columns 1A and 1B pass into a waste reservoir vessel or pass into the recovery vessel 25. The reservoirs 5, 6, 7, 8 and 9 are various solution reservoirs, and the solution (mobile phase) containing the material to be separated is stored in the reservoir 5, to be supplied to the selection valve 15 through the liquid feed pump 3. A column equilibration solution is stored in the reservoir 6, the wash solution is stored in the reservoir 7, the elution solution is stored in the reservoir 8, and a regeneration solution is stored in the reservoir 9. The selection valve 14 selects one of the reservoirs 6, 7, 8 and 9 to be in communication with the pump 4, so that the various solutions can be supplied to the selection valve 15 through the liquid feed pump 4.

The selection valve 15 is a valve for switching the solution flowing from the pump 3 side and the solution flowing from the pump 4 side to the column 1A or the column 1B so as not to select the same column at the same time when selecting the flow paths. For example, the switching valves 21 to 24 are controlled so that the solution flowing from the pump 4 side flows to the column 1B side when the solution flowing from the pump 3 side flows to the column 1A side. Meanwhile, the switching valves 21 to 24 are controlled so that the solution flowing from the pump 4 side flows to the column 1A side when the solution flowing from the pump 3 side flows to the column 1B side. Purified protein separated by the column 1A or 1B can be intermittently recovered by sending the purified protein to the recovery vessel 25 by switching valves 12 and 13 only when it is desired to be recovered. Incidentally, in order to monitor whether recovery is properly performed, it is possible to monitor chromatography by attaching an ultraviolet monitor 26 (a UV monitor) in the middle of a recovery line.

Although a case where four kinds of reservoirs 6, 7, 8 and 9 are used is illustrated, it is also possible to perform chromatography using more than four kinds of solutions. In this example, since the equilibration solution, the wash solution, the elution solution and the regeneration solution are needed as solutions required in adsorption chromatography, a configuration of minimum unit is described. When using more than four kinds of solutions, it is sufficient to use reservoirs and switching valves corresponding to the number of the solutions used, according to the configuration shown in FIG. 4. Even in this case, on/off control of the pumps, flow rates, switching of valves, and the like can be controlled by the control device such as the computer. Therefore, by using this device, it is possible to perform protein purification by fully automated continuous operation until a sample is exhausted after starting liquid feed of the sample.

The separation device shown in FIG. 5 is different from the separation device shown in FIG. 4, and the selection valve 14 and the pump 4 are for feeding the solutions stored in the reservoirs 6 and 7. Further, the separation device shown in FIG. 5 has the same configuration as the separation device shown in FIG. 4, except that it includes a selection valve 33 and pump 34 for feeding the solutions stored in the reservoirs 8 and 9, a selection valve 35 used for liquid feed to the separation column 1B, a selection valve 36 used for liquid feed to the separation column 1C, a switching valve 37 for controlling liquid feed to the separation column 1C, and a switching valve 32 connected to the separation column 1C through a pipe on the opposite side of the switching valve 37.

<Control Method and Column Design for Continuous Process>

Figure 6:
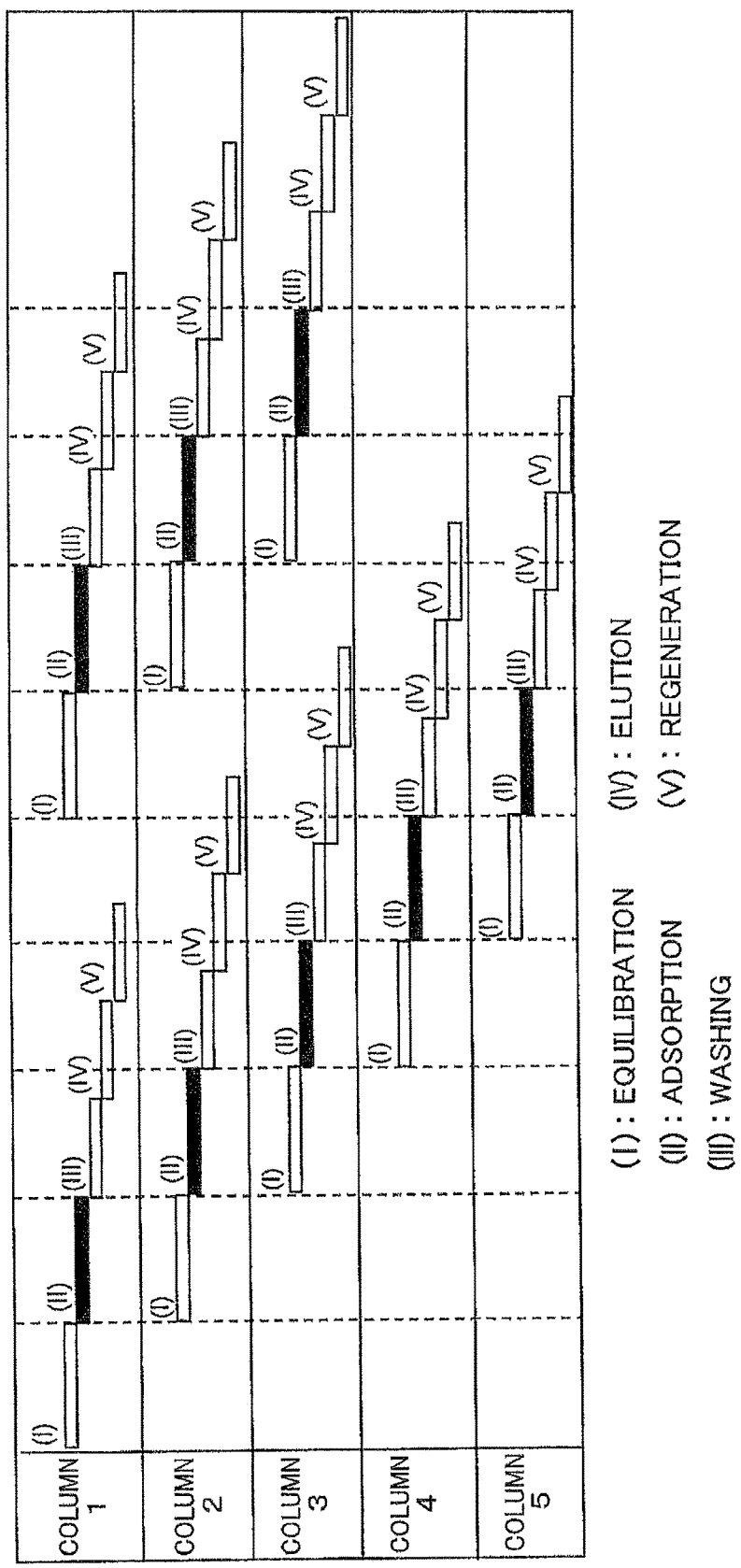
FIG. 6 is a diagram showing an example of processing steps of a continuous affinity purification device.

For example, separation and purification of the material using an affinity column generally includes steps of (I) column equilibration, (II) target material adsorption, (III) washing, (IV) target material elution, and (V) column regeneration. The sample solution is processed in (II) target material adsorption. In other words, other steps of (I), (III), (IV) and (V) are not steps for processing the sample solution. With this separation device, it is possible to continuously process the sample solution by shifting processing steps in a plurality of packed columns as shown in FIG. 6. Thus, it is possible to process a large volume of the sample solution efficiently in a short time, and thereby efficiently performing separation and purification of the target material. In addition, with this separation device, it is possible to use the same separation column repeatedly up to the usage count limit.

Further, when the separation column is divided into a plurality in a column bed height direction (in a linear flow rate direction of the sample solution), pressure loss applied to each column is reduced, and thus it is possible to reduce pressure load applied to the columns. Here, a total of column bed heights of the plural columns is set to a column bed height when the stationary phase having the volume capable of processing the entire volume of the mobile phase containing the material to be separated is a single column. Thus, it is possible to process a large volume of the sample solution efficiently in a short time, and thereby efficiently performing separation and purification of the target material.

In this separation device, when using two or more separation columns, it is preferable to design the separation device by considering that each separation column depends on the volume of the sample solution to be treated and a time required for each of the steps (I) to (V). Specific design method will be described below.

1. Method for Determining the Number of Columns

In order to continuously perform the processes (above-described (I) to (V)) for separating the material contained in the culture solution, it is necessary to perform the step of (II) target material adsorption by shifting time using two or more columns (see FIG. 6). Here, when the number of the columns is N, a column equilibration time is T1, a target material adsorption time is T2, a washing time is T3, a target material elution time is T4, and a column regeneration time is T5, it is generally possible to continuously process the culture solution by setting the number of the columns to satisfy Equation (1).

$$N \times T2 \geq (T1+T2+T3+T4+T5) \qquad \text{Equation (1)}$$

Meanwhile, each of times (I) to (V) can be determined as follows. Note that, the following method is an example, and they may be determined by other criteria.

Method for Determining Column Equilibration Time T1

The column equilibration time can be determined as a time required for baseline stabilization when monitoring the absorbance of the effluent in the column equilibration. Meanwhile, it may be determined as a time required until a liquid feed amount at the time of replacing the solvent becomes ten times of a column volume.

Method for Determining Target Material Adsorption Time T2

When a linear velocity of liquid feed to the column is determined, a time required for the target material adsorption can be determined by the following equation.

(adsorption time)=(column bed height)/(linear velocity)

Figure 7:
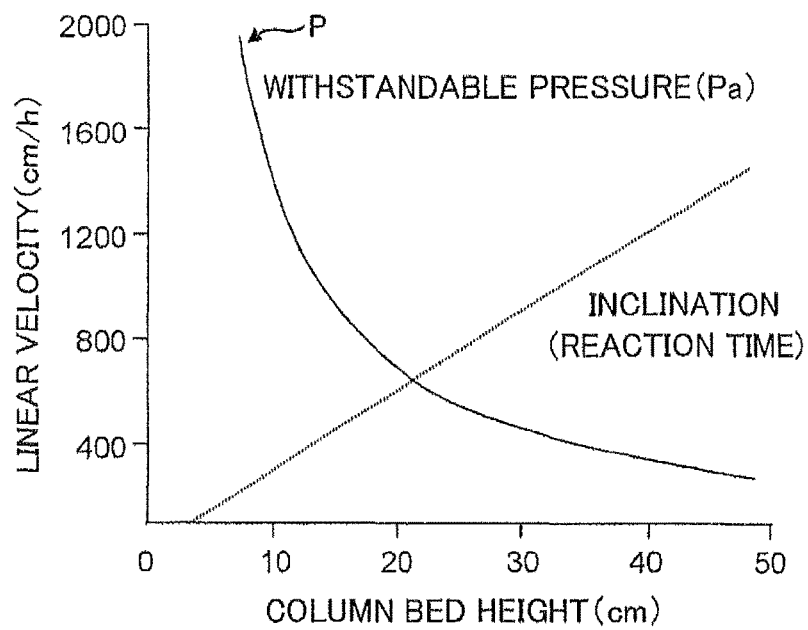
FIG. 7 is a diagram showing a relationship between a column bed height and a linear velocity.

The linear velocity can be determined as follows. The column bed height and the linear velocity have a relationship shown in FIG. 7, and a condition that the linear velocity is in a range of equal to or lower than an allowable pressure of the column (equal to or lower than a curve P in FIG. 7) must be satisfied. In this range, by measuring recovery rates of the antibody by experiments under conditions of various column bed heights and linear velocities, it is possible to determine the column bed heights and the linear velocities for maintaining a constant value (for example, 95%) of the recovery rate. Instead of the above-described recovery rate measurement, a dynamic binding capacity to be described below may be measured.

An experimental example of the linear velocity measurement will be described below. An appropriate linear velocity has been studied using a protein A column. After IgG sample is added under various linear velocity conditions, the column is washed with 1.88 column volumes (CV) of sodium phosphate (pH 7.0) containing 300 mM sodium chloride solution, and then a stepwise elution is performed with 6.31 CV of 20 mM sodium phosphate (pH 2.8) containing 300 mM sodium chloride solution. A recovery amount of IgG is quantitated in various linear velocities, and the recovery rate is derived by calculating a ratio with respect to the sample amount of IgG added. In this embodiment, a linear velocity for maintaining recovery rate of 90% or more is a proper linear velocity.

There are two kinds of carrier binding capacities, i.e., a maximum binding capacity and a dynamic binding capacity. The former indicates an upper limit amount of target molecules which can be recovered by the carrier, and the latter is a value to indicate how efficiently the target molecules can be recovered in a state where the sample to be purified flows. Since the carrier with high dynamic binding capacity can recover a lot of target molecules at a high flow rate, it can efficiently purify the target molecules in a short time. Meanwhile, the maximum binding capacity can be determined by monitoring the absorbance of the effluent after adding a standard protein solution to the column. Liquid feed is continued until the absorbance of the effluent is equal to that of the added sample, and the binding amount can be determined from "amount of eluted protein". The maximum binding capacity is not affected by the flow rate of the added sample.

Figure 8:
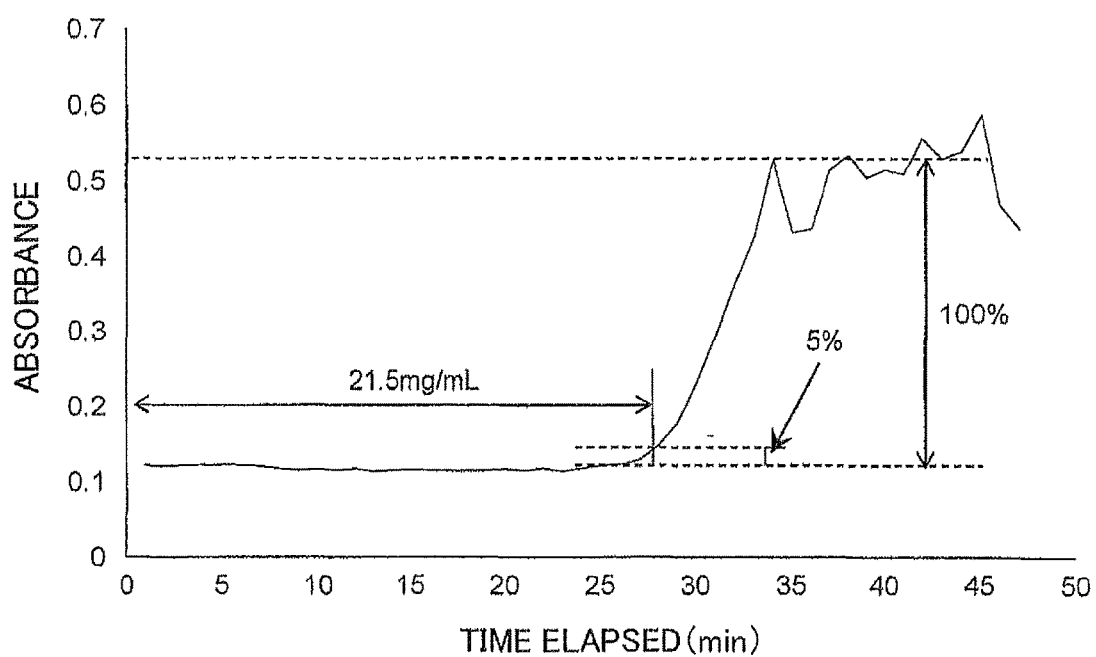
FIG. 8 is a diagram showing how to determine a dynamic binding capacity.

An experimental example of dynamic binding capacity measurement will be described below. The dynamic binding capacity is measured according to the following sequence. IgG of 10 mg/mL concentration diluted in PBS is fed 10 mL with a syringe pump at the linear flow rate of 500 cm/h. The absorbance of the solution is measured at an exit of the flow path. Results are shown in FIG. 8. In general, since the dynamic binding capacity is often assumed to be an amount of added protein when 5% of the amount of protein or the absorbance of the added sample is eluted, it is understood that the dynamic binding capacity is 21.5 mg/mL as shown in FIG. 8.

Incidentally, a method for determining the linear flow rate (cm/h) will be described below for reference.

$$\text{linear flow rate (cm/h)} = [\text{flow rate (mL/min)}] \times 60 / [\text{cross-sectional area (cm}^2\text{) of column}] = [Z \times 60 \times 4] / [\pi \times d^2]$$

(Z=flow rate, d=inner diameter (cm) of column)

Method for Determining Washing Time T3

Effects of washing can be confirmed by measuring pressures before and after washing. For example, before replacing elution buffer with the wash solution or after washing with the wash solution, by comparing pressures when ultrapure water flows after replacement with ultrapure water, a time until the pressure is reduced can be determined as the washing time. As another method, by measuring the absorbance of the effluent in a washing step, a time until the baseline is stabilized can also be determined as the washing time. Or, a time until the wash solution of a constant multiple (for example, 10 times) of the column volume flows can also be determined as the washing time.

Column washing must be studied in consideration of integrity/safety of product and lifetime of purification carrier. For the purpose of column washing, the following cleaning agents can be used. However, it is not limited to these cleaning agents, and other cleaning agents can be used. That is, guanidine hydrochloride can be used as the cleaning agent. Guanidine hydrochloride is characterized by destroying hydrophobic interaction, to dissolve precipitated denatured protein. Further, as the cleaning agent, organic solvent such as isopropanol can be used. The organic solvent is characterized in that it is difficult to remove a raw material in which lipids and hydrophobic impurities has been removed or precipitated. Furthermore, as the cleaning agent, sodium hydroxide can be used. Sodium hydroxide is characterized by solubilizing precipitated protein, solubilizing lipids by alkaline hydrolysis, removing nucleic acid from the carrier, having bactericidal activity, and degrading protein ligand. Among the above-described cleaning agents, sodium hydroxide is especially suitable because it is effective for washing, sterilization, pyrogen inactivation, and virus inactivation.

Target Material Elution Time T4

The elution time can be determined as a time until the absorbance of the effluent containing antibody is reduced to return to the baseline from flow beginning of the elution solution after adsorption of the antibody on the column.

Column Regeneration Time T5

As an example, the column regeneration time can be determined as a time required to feed 15 column volumes (CV) of ultrapure water after removing metal ions by feeding 10 CV of 20 mM phosphate buffer, 0.5 M NaCl solution, 50 mM EDTA solution (pH 7.4). When the column is severely contaminated, the column regeneration time can be determined as a time required to return the column to neutral by feeding more than 15 CV of neutral buffer, after washing by slowly feeding additional 5 CV of 1 M NaOH solution.

When simply flowing ultrapure water after washing with acid or alkaline solution, acid or alkali remains in the column, to damage the carrier in some cases, and thus it is possible to reduce damage to the carrier by putting the washing step with NaCl after washing with acid or alkali.

2. Method for Determining Column Volume

When target material concentration in the culture solution is Ct, volume of the culture solution per one batch is Vb, dynamic adsorption amount of the target material per unit volume of column is Am, volume per one column is Vc, the number of the columns is N, and the number of column reuse is R, a relationship of Equation (2) is established.

$$Ct \cdot Vb \leq Am \cdot Vc \cdot R \cdot N \qquad \text{Equation (2)}$$

It is possible to satisfy Equations (1) and (2) by increasing the number of the columns N, however, since control system of the purification device is complicated as the number of the columns N increases, it is desirable that the number of the columns N is a minimum number while satisfying Equations (1) and (2). The stationary phase in the column is usually used repeatedly, however, the lifetime (lifetime count) is determined as the number of reuses until protein A or the like in the stationary phase is gradually degraded (desorbed or denatured) by alkali treatment with NaOH or the like in the regeneration step, recovery amount of the target material is gradually reduced, and desired recovery amount cannot be obtained. When the lifetime is different for each stationary phase, the lifetime may be determined as a time until a certain recovery amount determined by a user is not obtained while monitoring the recovery amount for each use, or may be determined as the number of reuses guaranteed by a manufacturer. Since R is the number of reuses (lifetime) of the column, the column volume is (1/R) of a normal column.

3. Division of Column

Figure 9A:
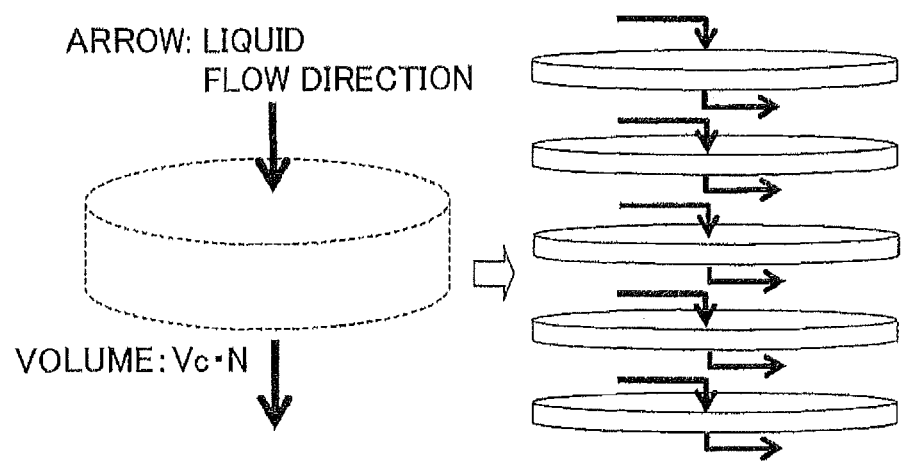
FIG. 9A is a diagram showing an example of division of the column.
Figure 9B:
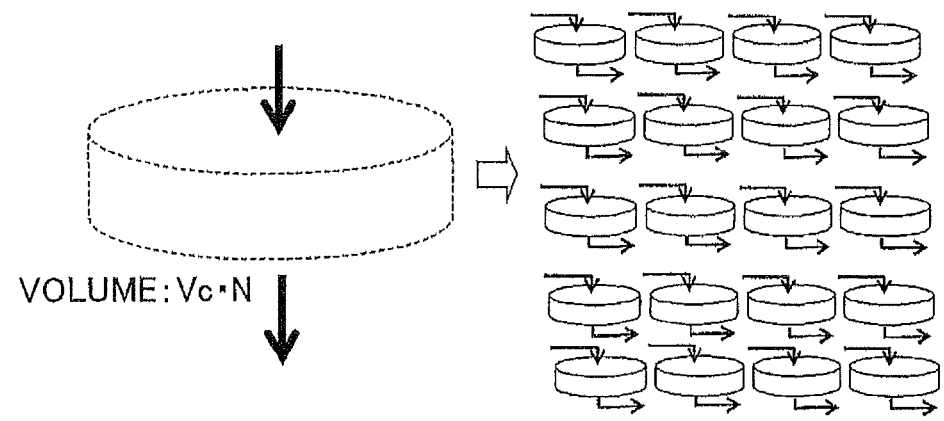
FIG. 9B is a diagram showing another example of division of the column.

Necessary column volume is the product of the volume per one column Vc and the number of the columns N. When dividing a column having a volume of Vc·into N, the pressure loss of the columns, which are divided to have the same column bed heights and 1/N of the column cross-sectional area, is larger than that of the column before the division. Therefore, it is desirable that the column is divided into at least two in the column bed height direction. The column bed height and the cross-sectional area may be divided so that the pressure loss is less than a design upper limit (see FIGS. 9A, 9B). In FIG. 9A, the column is divided in the height direction with the same cross-sectional area. FIG. 9B shows a case where the height and the cross-sectional area are divided and the divided columns are consistent with specification of commercially available column.

4. Column Material (Filler and Column Holder)

As described above, the separation column is filled with the stationary phase having the volume capable of processing the entire volume of mobile phase to be processed. Therefore, after using the separation column for a given batch, it is possible to process next batch using a new separation column by replacing the separation column itself. In particular, when using plural separation columns as described above, it is possible to reduce pressure applied to the columns even if the mobile phase to be processed has a large volume. Therefore, acrylamide, polypropylene, high density polyethylene, polyethylene terephthalate or the like, which is used as a disposable material in other fields, can be a material of the column holder in this case. Note that, it is also possible to use the separation column with column holder made of glass or stainless, which has been conventionally used.

Further, as a material of the stationary phase, it is possible to use any material which has been conventionally used. For example, either one or a combination of agarose and silica gel can be used. Furthermore, there is no particular limitation to a ligand capable of specifically capturing the material to be separated, and for example, protein A, protein G, or thiophilic interaction can be used.

<Example of Application to Biopharmaceutical Purification Step>

Figure 10:
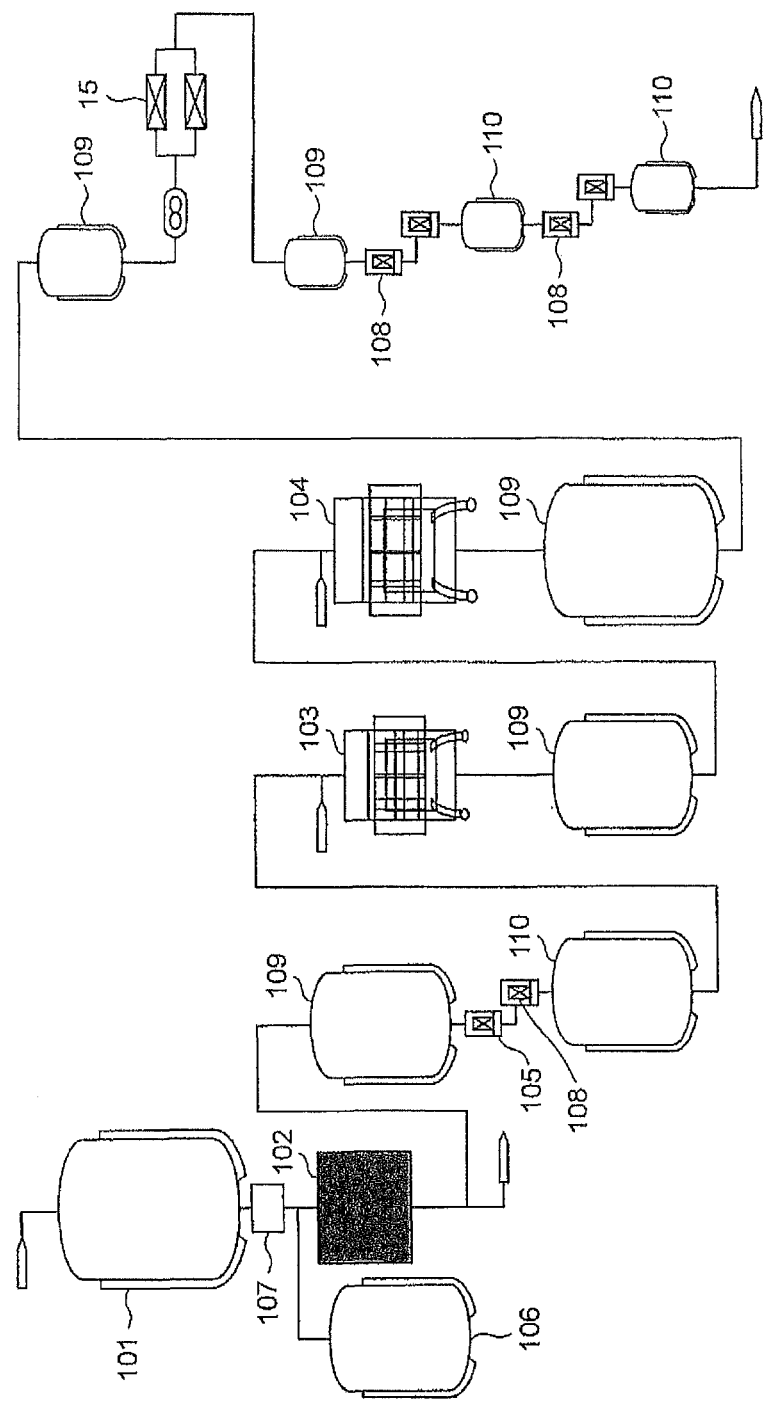
FIG. 10 is a diagram showing a purification system applied to a biopharmaceutical production plant.

A system in which the separation device according to the present invention is applied to the biopharmaceutical purification step is shown in FIG. 10. The system shown in FIG. 10 includes a culture medium tank 101 filled with a culture solution in which cells secreting or producing biopharmaceuticals such as antibodies are cultured, an affinity column 102 having the stationary phase for specifically capturing the antibody to be separated, and an eluent tank 106 filled with the eluent for eluting the antibody captured by the stationary phase. Further, in the system shown in FIG. 10, a fraction tank 109, a UF filter device 105, a sterilizing filter 108, a receiving tank 110, an anion exchange column 103, a fraction tank 109, a cation exchange column 104, and a fraction tank 109 are sequentially provided downstream of the affinity column 102. Furthermore, in the system shown in FIG. 10, a cooling device 107 is provided upstream of the affinity column 102.

First, the culture solution containing biopharmaceuticals such as antibodies are clarified by removing components such as cells by centrifugation or the like. Then, the biopharmaceuticals such as antibodies of interest are recovered using the system shown in FIG. 10. In this capture step, the affinity column 102 continuously processes the culture solution according to a process table shown in FIG. 6. During this time, the filler in the affinity column 102 can be reused according to the process table shown in FIG. 6. The stationary phase filled in the affinity column 102 has a volume capable of processing an entire volume of the culture solution, and the entire volume of the culture solution is preferably an available upper limit volume. Here, the available upper limit volume is a maximum passing volume of the mobile phase when separation performance of the stationary phase can be maintained.

Culture sample solution obtained through the capture step is filled into a vial through the intermediate purification and the polishing. After one batch is completed for the culture solution, the affinity column 102 can be removed, to be subjected to incineration as it is. As for next culture solution, it is possible to easily perform next preparation by connecting a new affinity column 102 to a line. Thus, with the present invention, when the column is deteriorated, it is not necessary to replace the filler, and it is possible to reduce the processing time. Further, with the present invention, special devices or procedures are not required to fill a large amount of filler into a large column, and it is possible to very easily process a large volume of the culture solution.

REFERENCE SIGNS LIST

1: column
2: column
3: liquid feed pump
4: liquid feed pump
5 to 9: reservoir
10 to 13: switching valve
14, 15: selection valve
21 to 24: switching valve
31: column
32: switching valve
33: selection valve
34: liquid feed pump
35, 36: selection valve
37: switching valve
38: switching valve
39: computer
40: control device
41 to 43: switching valve
44 to 46: UV detector, control device
101: culture medium tank
102: affinity column
103: anion exchange column
104: cation exchange column
105: UF filter device
106: eluent tank
107: cooling device
108: sterilizing filter
109: fraction tank
110: receiving tank

The invention claimed is:

1. A method of separation with a separation device comprising:

determining a number of plural columns and a total column volume to be provided in the separation device is provided in an amount satisfying the following equations:

$$N \times T2 \geq (T1+T2+T3+T4+T5), \text{ and}$$

$$Ct \cdot Vb \leq Am \cdot Vc \cdot R \cdot N,$$

where N is a number of plural columns, T1 is an equilibrium time of the separation column, T2 is an adsorption time of the material to be separated, T3 is a washing time, T4 is an elution time of the material to be separated, T5 is a regeneration time of the separation column, Ct is a concentration of the material to be separated in the mobile phase, Vb is a volume of the mobile phase per one batch, Am is a dynamic adsorption amount of the material to be separated per unit volume of the separation column, Vc is a volume of the stationary phase per one separation column, and R is a number of reuses of one separation column, one column volume being determined as 1/R;

providing a separation device composed of N plural columns provided with a stationary phase having a total volume sized (Vc·N) to process an entire volume of a selected mobile phase Vb containing a selected material to be separated.

2. The method of claim 1, further comprising:

providing a plurality of pipes respectively connected to each of the plural columns;

providing a plurality of switching valves respectively provided on the plurality of pipes; and providing a computer for controlling communication between the pipes by the plurality of switching valves.

* * * * *